United States Patent [19]

Sidebottom et al.

[11] 4,221,129

[45] Sep. 9, 1980

[54] HUMIDITY SENSOR

[75] Inventors: Donald L. Sidebottom; Richard L. Stottmann, both of Louisville, Ky.

[73] Assignee: General Electric Company, Louisville, Ky.

[21] Appl. No.: 36,895

[22] Filed: May 7, 1979

[51] Int. Cl.³ .............................................. G01W 1/00
[52] U.S. Cl. ................................................. 73/336.5
[58] Field of Search ....................... 73/336.5, 335, 29; 200/61.06

[56] References Cited

U.S. PATENT DOCUMENTS

| | | |
|---|---|---|
| 3,230,402 | 1/1966 | Nightingale et al. . |
| 3,368,755 | 2/1968 | Smith et al. . |
| 3,608,376 | 9/1971 | Fenner ................................ 73/336.5 |
| 4,163,384 | 8/1979 | Blakemore .............................. 73/29 |

Primary Examiner—Gerald Goldberg
Assistant Examiner—Joseph W. Roskos
Attorney, Agent, or Firm—Frederick P. Weidner

[57] ABSTRACT

A humidity sensor utilizing the electrical output of a piezoelectric crystal held in compressive stress at one end of a lever arm, the fulcrum at the other end of the lever arm consisting of a flexure hinge of moisture sensitive material with a thickness under 10 mils. The crystal is nested in a frame to which the flexure hinge is attached and the frame hinge and lever arm may be molded out of the same moisture sensitive material. A moisture sensitive form of Nylon may be used for the flexure hinge. The signal output of the crystal is a function of the compressive stress which in turn varies as the modulus of the flexure hinge varies as caused by changes in ambient humidity.

8 Claims, 5 Drawing Figures

4,221,129

HUMIDITY SENSOR

BACKGROUND OF INVENTION

The present invention relates to a novel humidity sensor and control apparatus useful therewith.

Humidity sensors are fundamentally based on the concept that changes in atmospheric moisture can cause dimensional changes in certain well known moisture sensitive materials such as cellulose, hair strands, animal horn and certain synthetic materials such as nylon. These dimensional changes are then converted by any of a variety of mechanical, electromechanical or pneumatic devices into a humidity reading or a control effect, as needed. Such devices are generally expensive to manufacture and very often are quite delicate to handle.

In the appliance industry there is a need for an inexpensive, rugged, humidity sensor that can be used to control the operation of the appliance for most energy efficient usage. For example, it is common practice in refrigerators to provide heaters in the breaker frames to raise the temperature of the surface adjacent the compartment opening to avoid moisture formation or sweating on the breaker frame. It is well known that sweating on refrigerator breaker frames tends to be a problem only in high humidity environments. As a result, a manual switch is provided to permit the appliance to turn off the anti-sweat heaters when they are not needed. The use of a humidity sensor to perform this control function automatically has long been considered, but a practical barrier to its adoption has been the cost and complexity involved in the use of known humidity sensors for this purpose.

OBJECTS AND BRIEF SUMMARY OF INVENTION

It is, therefore, an object of the invention to provide a simple inexpensive humidity sensor that is rugged in construction.

It is a further object of the invention to provide a humidity sensor that is readily adapted to operate electronic control devices.

It is a still further object of the invention to provide a humidity sensitive control apparatus for an appliance that is useful in controlling the energy usage of the appliance, such as by controlling the cycling of a refrigerator evaporator defrost operation or by controlling the operation of anti-sweat heaters.

Accordingly, there is provided a humidity sensor comprising a piezoelectric crystal held in compressive stress by one end of a substantially inflexible lever arm, the fulcrum for the lever arm consisting of a flexure hinge of moisture sensitive material with a thickness of less than 10 mils. The modulus of elasticity of the flexure hinge varies with moisture content thereby varying the compressive force on the crystal exerted by the lever arm. In one preferred form of the invention, the crystal is nested in a frame to which the lever arm is attached at its fulcrum end, and the entire frame and lever arm combination is molded out of the same moisture sensitive material, for example nylon. The voltage output of the stressed crystal can be readily calibrated to correspond to relative humidity within a desired range of temperature and moisture conditions.

DETAILED DESCRIPTION

Figure 1:
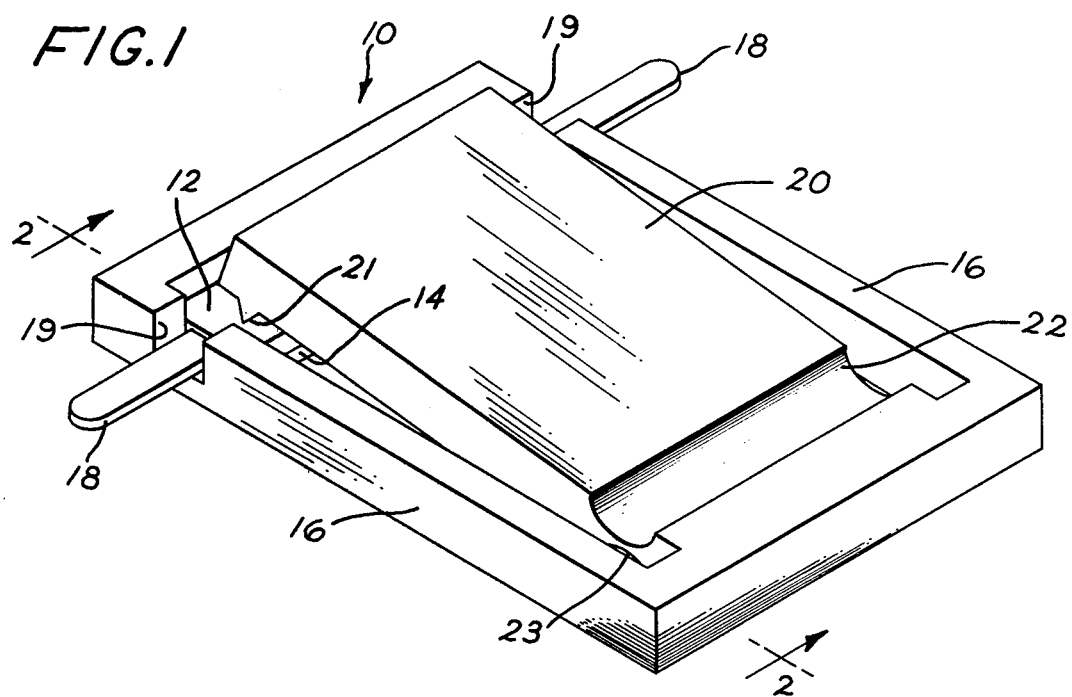
FIG. 1 is a perspective view of a humidity sensor constructed in accordance with the present invention.
Figure 2:
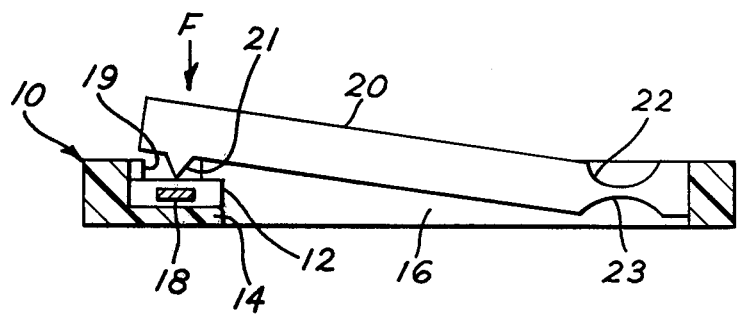
FIG. 2 is a cross-section view of the FIG. 1 sensor illustrating structural details thereof.

Referring to FIGS. 1 and 2, the humidity sensor 10 shown therein includes a piezoelectric crystal 12 lying on a shelf 14 nested within a frame 16. Crystal 12 may be comprised of any well known crystal material such as quartz, tourmaline, or Rochelle salt, which generates a surface charge when subjected to a stress on the surface of the crystal. Terminals 18 are attached to either end of the crystal and provide for connection to an electrical circuit whereby the voltage variations on terminals 18 resulting from surface charge variations on crystal 12 can be converted in well known manner to a useful signal output representative of the stress variations on the crystal.

Crystal 12 is held in compressive stress by one end of an elongated lever arm 20, the other end of arm 20 being attached to frame 16 by means of a flexure hinge 22 comprised of a moisture sensitive material such as moisture sensitive nylon or cellulose acetate. Although, for the most part, the dimensions of the sensor 10 are not particularly critical, it is nevertheless preferred, for reasons discussed later, that the thickness of flexure hinge 22 at its thinnest point 23 be less than 10 mils thick and, most preferably, on the order of between 2-5 mils thick. For most economical production, the frame, lever arm and flexure hinge of sensor 10 may be integrally molded entirely of the same material. The piezoelectric crystal 12 may then be inserted in place within frame 16 under the lever arm 20 with terminals 18 nested in receiving slots 19 formed in frame 16. To maximize the stress effect on the surface of crystal 12, and therefore to maximize its sensitivity to variations in force F, the end of lever arm 12 is preferably shaped with an elongated pointed ridge or stylus 21, the pointed apex of which is pressed against the surface of crystal 12. As is known in the art, the modulus of elasticity of materials such as referred to herein will vary inversely with moisture absorption. Moisture absorption, in turn, is affected by the atmospheric moisture or relative humidity of the environmental air in which the sensor is located. In the sensor of FIGS. 1 and 2, the magnitude of the leverage force F applied to crystal 12 will be proportional to the modulus of elasticity of the material used in flexure hinge 22, and since this modulus will vary with changes in atmospheric moisture (relative humidity), the force F will vary causing the voltage output of crystal 12 to provide a measure of changes in percent relative humidity (FIG. 4).

Figure 3:
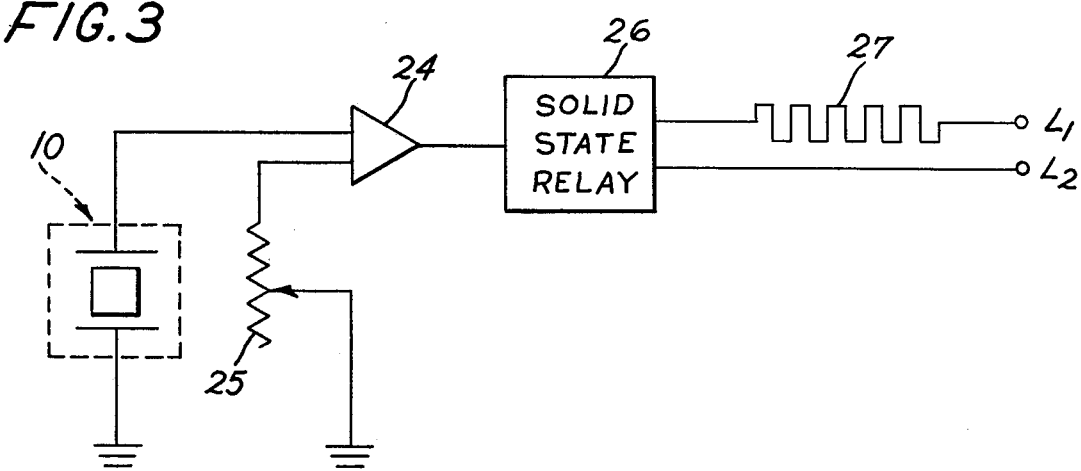
FIG. 3 is a circuit diagram for a digital form of control apparatus embodying the present invention to control the operation of refrigerator anti-sweat heaters.

Referring now to FIG. 3, there is shown one form of control circuit which may be used to derive a control effect from the humidity sensor 10. To this end, the terminals 18 of the crystal 12 are connected across one input of a comparator amplifier circuit 24. The other input of comparator 24 is connected to a variable resistor 25 which serves to establish a manually settable threshold voltage which can be calibrated to correspond to a predetermined level of atmospheric moisture sensed by the humidity sensor 10. When the sensor input to comparator 24 varies beyond this threshold level, the output of comparator 24 changes state and causes a solid state relay 26 to change its switch state. In the FIG. 3 circuit, relay 26 is coupled in circuit with anti-sweat heaters 27, the latter typically being mounted inside the breaker frame of a refrigerator as aforesaid. In this way, anti-sweat heaters 27 can be turned on or off automatically depending on the humidity level of the room as sensed by the humidity sensor 10. Variable resistor 25 may be internally mounted inside the refrigerator cabinet structure after being set at the factory or it may be connected to an external control knob accessible to the appliance owner so as to be adjustable by the owner for varying conditions in the room as, for example, might result from seasonal changes in the atmosphere. This variable resistor could also be non-adjustable for the consumer.

Alternatively, sensor 10 may be mounted within the vegetable pan volume in the fresh food section of the refrigerator. It can then be used to control a solenoid operated valve which may be located, for example, in the shelf above the vegetable pan so as to allow any excess moisture in the vegetable pan to be vented into the fresh food compartment, thus minimizing deterioration of vegetable quality caused by the excess moisture.

Figure 4:
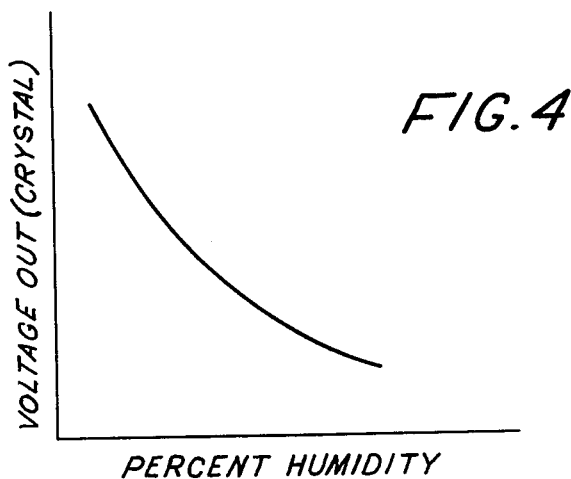
FIGS. 4 and 5 are graphs useful in explaining the operation of the present invention.
Figure 5:
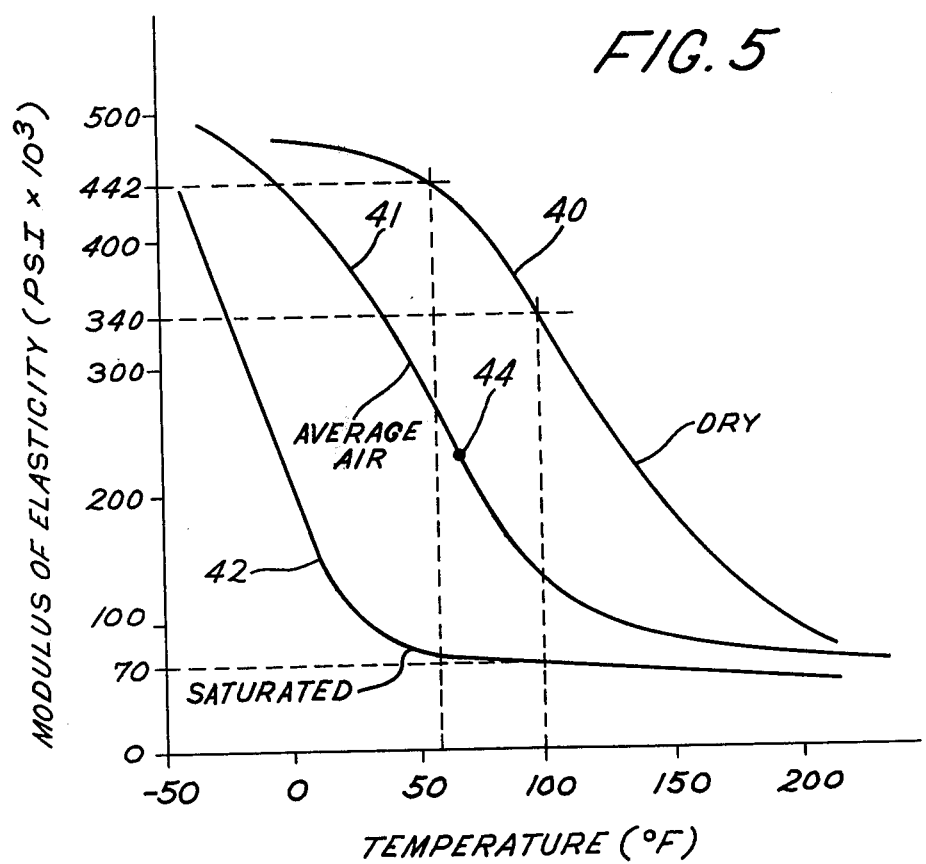

Referring now to FIGS. 4 and 5, the voltage output of crystal 12 will vary as the compressive force F varies with changing humidity, the mechanism of the force variation being the changing modulus at flexure hinge 22 caused by varying degrees of moisture absorption. Since the modulus at and near the surface of the material will be the first to respond to changes in atmospheric moisture, the sensitivity in terms of response time and hysteresis effect is maximized in sensor 10 by making the hinge thickness desirably less than 10 mils and preferably in the range of 2-5 mils thick, as previously mentioned.

Ideally, a material whose modulus is sensitive only to moisture variations would be employed in flexure hinge 22. For cost and availability reasons, however, it may be preferred to use materials which are, at least to some measurable extent, jointly responsive to moisture and temperature, such as Type 6 and 6/6 nylon available from E. I. DuPont de Nemours & Co. under the trademarks ZYTEL 211 and ZYTEL 101. FIG. 5 shows a family of curves illustrating the manner in which the modulus of this material varies both as a function of temperature and moisture content, where curve 40 corresponds to the dry nylon as molded, curve 41 represents the nylon exposed to air with average moisture content and curve 42 represents the nylon in a fully moisture saturated condition. While there are very substantial modulus variations as a function temperature over the full illustrated range of −50° F. to 200° F., there is actually relatively little temperature caused modulus change in the limited temperature ranges encountered in the home. Considering the fairly conservative, i.e. broad, temperature range of 60° F. to 100° F., it can be seen from FIG. 5 that the effect of modulus variations as measured on the dry material is a relatively small proportion of the modulus that can occur for different atmospheric moisture conditions within this temperature range. Moveover, under practical conditions, the modulus variations within this temperature range are even more pronounced when one considers that higher temperatures tend to be accompanied by higher relative humidity conditions, as seen by representative curve 43. Thus, the comparator 24 of the FIG. 3 circuit can be set to respond to voltage output which is representative of a modulus condition for the material involved corresponding to point 44 of curve 41 which can cause anti-sweat heaters 27 to be turned on for most if not all normal high humidity conditions even though the material may be jointly responsive to temperature and humidity variations. When used as a vegetable pan moisture sensor, as described above, the sensor 10 is even more directly responsive to moisture variations since the temperature within the refrigerator is normally maintained at a fairly constant level.

While there has been described what at the present time is considered to be a preferred embodiment of the invention, it will be obvious to those skilled in the art that various changes and modifications may be made therein without departing from the invention. It is, therefore, intended by the appended claims to cover all such changes and modifications as fall within the true spirit and scope of the invention.

What is claimed is:

1. A humidity sensor comprising a piezoelectric crystal held in compressive stress by one end of an elongated lever arm, the other end of which comprises a fulcrum section consisting of a substantially thin flexure hinge of moisture sensitive material.

2. The humidity sensor of claim 1 in which the thickness of the flexure hinge is less than 10 mils at its thinnest point.

3. The humidity sensor of claim 2 in which said hinge thickness is approximately in the range of 2-5 mils.

4. The humidity sensor of claim 1 in which the lever arm is substantially inflexible.

5. The humidity sensor of claim 1 in which the crystal is nested within a frame and the flexure hinge is attached to the frame at a point remote from the location of the crystal.

6. The humidity sensor of claim 5 in which the frame, lever arm, and flexure hinge are integrally molded of the same material throughout.

7. The humidity sensor of claim 1 or 6 in which the material used for at least the flexure hinge is moisture sensitive nylon.

8. The humidity sensor of claim 1 or 6 in which the material used for at least the flexure hinge is cellulose acetate.

* * * * *